(12) United States Patent
Alok et al.

(10) Patent No.: US 8,183,377 B2
(45) Date of Patent: May 22, 2012

(54) PROCESS FOR THE PREPARATION OF IMIDAZOPYRIDINES

(75) Inventors: Saxena Alok, Mumbai (IN); Rajiv R. Sakhardande, Mumbai (IN); Crasta Santosh, Mumbai (IN); Hemant Chaudhari, Mumbai (IN); Madhav Jadhay, Mumbai (IN)

(73) Assignee: Elder Pharmaceuticals Ltd., Navi Mumbaie, Maharashtra ( * ) Notice: Subject to any disclaimer, the term of this patent is extended or adjusted under 35 U.S.C. 154(b) by 489 days.

(21) Appl. No.: 11/990,880

(22) PCT Filed: Dec. 2, 2005

(86) PCT No.: PCT/IN2005/000395
§ 371 (c)(1), (2), (4) Date: Oct. 20, 2009

(87) PCT Pub. No.: WO2007/023504
PCT Pub. Date: Mar. 1, 2007

(65) Prior Publication Data
US 2010/0036129 A1    Feb. 11, 2010

(51) Int. Cl.
*C07D 471/04*  (2006.01)

(52) U.S. Cl. .................................................... 546/121

(58) Field of Classification Search ............... 546/121
See application file for complete search history.

(56) References Cited

U.S. PATENT DOCUMENTS
6,384,226 B2 *    5/2002    Castaldi .................. 546/121

FOREIGN PATENT DOCUMENTS
EP    1172364 A1    1/2002
WO    WO-0214306 A1    2/2002

* cited by examiner

*Primary Examiner* — Janet Andres
*Assistant Examiner* — Niloofar Rahmani
(74) *Attorney, Agent, or Firm* — Schwegman, Lundberg & Woessner, P.A.

(57) ABSTRACT

A process for the preparation of imidazopyridines of formula (I), comprising reacting 6-methyl-2-(4-methylphenyl)imidazo[1,2-a]pyridine with oxalyl chloride, followed by conversion of the chloride to oxoacetic acid, and further to compound of Formula (I).

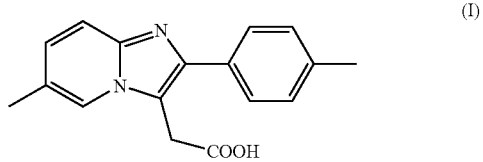

23 Claims, No Drawings

PROCESS FOR THE PREPARATION OF IMIDAZOPYRIDINES

RELATED APPLICATIONS

This application is a U.S. National Stage filing under 35 U.S.C. 371 from International Application No. PCT/IN2005/000395 filed Dec. 2, 2005, published on Mar. 1, 2007 as WO 2007/023504A1, which claims priority from Indian Application No. 999MUM/2005 filed August 24, 2005; which applications and publication are incorporated herein in their entirety and made a part hereof.

FIELD OF INVENTION

The present invention relates to a process for preparing imidazopyridines useful as intermediates in the preparation of ketones, lactams and pharmaceutical active ingredients e.g. N,N-dimethyl-6-methyl-2-(4-methylphenyl)imidazo[1,2-a]pyridine-3-acetamide (zolpidem).

BACKGROUND OF THE INVENTION

U.S. Pat. No. 4,382,938 suggests a process for the preparation of zolpidem by reacting (6-methyl-2-p-tolyl-imidazo[1,2-a]pyridin-3-yl)acetic acid (zolpidic acid) with dimethyl amine in the presence of carbonyldiimidazole. Large scale production with carbonyldiimidazole is not viable as carbonyldiimidazole is very expensive, toxic, allergenic and hygrocopic.

Additional methods for making various imidazopyridines are disclosed by Schmitt et. al, Aust. J. Chem., 1997, 50, 719-725. Among them is the reaction of certain 2-phenylimidazo[1,2-a]pyridines with freshly distilled ethyl glyoxylate to form ethyl 2-hydroxy-2-(2'-phenylimidazo[1,2-a]pyridin-3'-yl)acetate. This compound is reduced by adding phosphorus tetraiodide in dichloromethyl to form ethyl 2-(2'-phenylimidazo[1,2-a]pyridin-3'-yl)acetate.

EP1038875 describes the use of ethyl glyoxylate is not convenient for a commercial scale production. Also phosphorus tetraiodide is expensive, not readily available and produces iodine- and phosphorus-containing wastes. The '875 patent describes a method of preparing imidazopyridines of formula (I)

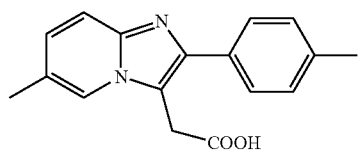
(I)

by reacting 6-methyl-2-(4-methylphenyl)imidazo[1,2-a]pyridine of formula (II) with glyoxylic acid or a compound of formula (V)

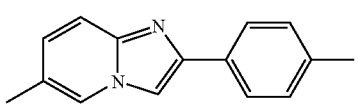
(II)

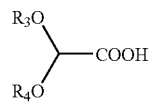
(V)

Where $R_3$ and $R_4$ each independently represent hydrogen or a lower alkyl to form a compound of formula (VI)

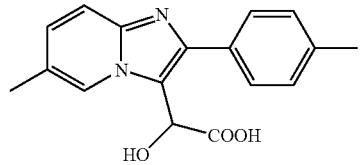
(VI)

and further removing the alpha hydroxyl group of (VI) with a hydrogenolysis agent in the presence of a hydrogenolysis catalyst to form (I). This method involves the use of expensive hydrogenolysis catalyst selected from the group consisting of palladium, platinum and rhodium. The use of formic acid, phosphonic acid and phosphinic acid as hydrogenolysis agent do not make the process of EP1038875 environment friendly.

The synthetic route for the preparation of compound of formula (I) is disclosed in EP1172364, which involves reacting a 2-phenyl-imidazo[1,2-a]pyridine of formula (II) with an oxalate, followed by reduction.

WO0214306 describes a method of preparing imidazopyridines of general formula (VI)

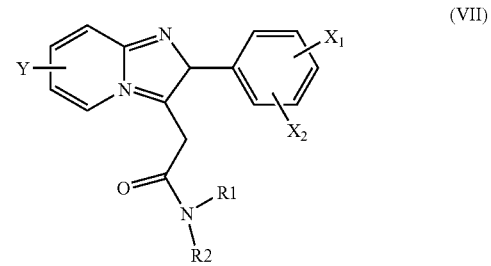
(VII)

in which: Y denotes H, halogen or $C_{1-4}$ alkyl group, $X_1$ and $X_2$ denote, independently of each other, hydrogen, a halogen or a $C_{1-4}$ alkoxy, $C_{1-6}$ alkyl, $CF_3$, $CH_3S$, $CH_3SO_2$ or $NO_2$ group and R1 and R2 denote independently of each other, H or a $C_{1-5}$ alkyl group, with the proviso that R1 and R2 do not both denote hydrogen or salts thereof by reacting compound of general formula (VIII)

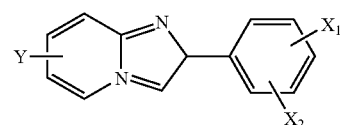
(VIII)

with a compound of general formula (IX)

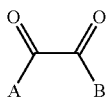
(IX)

in which A denotes a halogen and B denotes a halogen, a C$_{1-4}$ alkoxy or an NR1R2 to form a compound of general formula (X).

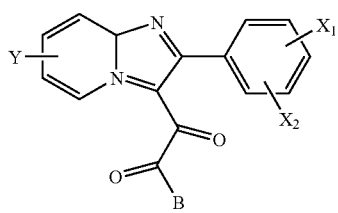
(X)

If B denotes a halogen or a C$_{1-4}$ alkoxy, the compound of formula (X) is reacted with NHR1R2 to form compound of formula (VI).

The present invention relates to a more efficient and commercially viable process for preparing compounds of formula (I).

SUMMARY OF THE INVENTION

In accordance with the present invention, compounds of formula (I) can be prepared as follows:
a) Reacting 6-methyl-2-(4-methylphenyl)imidazo[1,2-a]pyridine of formula (II) with oxalyl chloride to form (6-methyl-2-p-tolyl-2,3-dihydro-imidazo[1,2-a]pyridin-3-yl)-oxoacetyl chloride of formula (III);

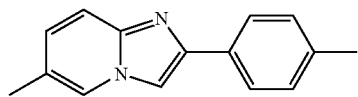
(II)

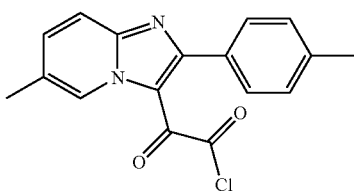
(III)

b) Converting the chloride of formula (III) to (6-methyl-2-p-tolyl-2,3-dihydro-imidazo[1,2-a]pyridin-3-yl)-oxoacetic acid of formula (IV) or its salt; and

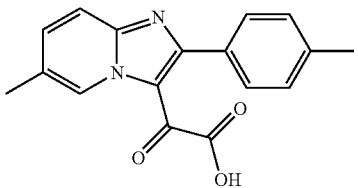
(IV)

c) Reacting the acid of formula (IV) or its salt with hydrazine in presence of glycols and a base.

In accordance with the present invention, compounds of formula (IV) can be prepared as follows:
a) reacting 6-methyl-2-(4-methylphenyl)imidazo[1,2-a]pyridine of formula (II) with oxalyl chloride to form (6-methyl-2-p-tolyl-2,3-dihydro-imidazo[1,2-a]pyridin-3-yl)-oxoacetyl chloride of formula (III); and

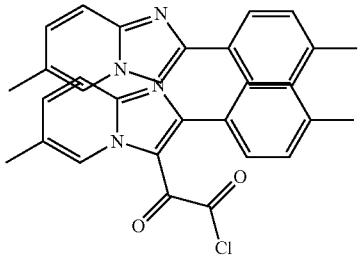
(II)

(III)

b) converting the compound of formula (III) to (6-methyl-2-p-tolyl-2,3-dihydro- imidazo[1,2-a]pyridin-3-yl)-oxoacetic acid of formula (IV) or its salt.

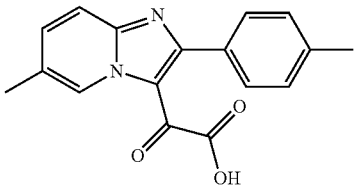
(IV)

The present invention further provides a compound, 6-methyl-2-p-tolyl- 2,3-dihydro-imidazo[1,2-a]pyridin-3-yl)-oxoacetic acid, having formula (IV) or its salt.

(IV)

DETAILED DESCRIPTION OF THE INVENTION

The starting compound of formula (II) was prepared according to the method described in british patent 991589. Oxalyl chloride used in the process is commercially available. According to the process of the present invention (6-methyl-2-p-tolyl-imidazo[1,2-a]pyridin-3-yl)acetic acid of formula (I) is obtained as follows:
a) reacting 6-methyl-2-(4-methylphenyl)imidazo[1,2-a]pyridine of formula (II) with oxalyl halide, preferably oxalyl chloride to form (6-Methyl-2-p-tolyl-2,3-dihydro-imidazo[1, 2-a]pyridin-3-yl)-oxo-acetyl chloride of formula (III);
b) converting chloride of formula (III) to (6-Methyl-2-p-tolyl-2,3-dihydro-imidazo[1,2-a]pyridin-3-yl)-oxo-acetic acid of formula (IV) or its salt; and c) reacting the acid of formula (IV) or its salt with hydrazine in presence of glycols and a base.

Typically compound of formula (II) is reacted with oxalyl chloride in presence of a solvent and a base at a temperature of about 15-30° C. The solvent is selected from ethylene dichloride, methyl tert-butyl ether, methylene dichloride, hexane and toluene, preferably ethylene dichloride and methylene dichloride and more preferably ethylene dichloride. The base is selected from triethylamine, potassium bicarbonate, sodium bicarbonate, potassium carbonate or sodium carbonate, preferably triethylamine.

The conversion of the chloride of formula (III) to oxo acetic acid of formula (IV) is preferably carried out by reacting (II) with water. Further a salt can also be prepared of (IV) by reacting (III) with water and a base. The base is preferably selected from alkali and alkaline earth metal hydroxides or carbonates. The alkali and alkaline earth metal hydroxides or carbonates are selected from sodium hydroxide, potassium hydroxide, sodium carbonate, potassium carbonate and the like. The glycols used in step c are selected from ethylene glycol and diethylene glycol.

From the zolpidic acid of formula (I), zolpidem can be readily made by methods of amidation that are well known in the art. For example, the acid of formula (I) can be reacted with an amidation agent either directly or after activation of the intermediate into an acylchloride, an anhydride, an activated ester, or an activated amide. The amidation reagent includes an amine. Typically, an amine is used as the amidation reagent in the presence of carbonyldiimidazole. A preferred amidation agent is dimethylamine.

The zolpidic acid of formula (I) when isolated, typically has a purity of at least 95%, preferably at least 97%, and more preferably at least 98%, without the need to perform a special purification step. Such high purity is advantageous for commercial scale production.

The invention will now be further described by the following non-limiting examples.

EXAMPLE 1

(6-Methyl-2-p-tolyl-2,3-dihydro-imidazo[1,2-a]pyridin-3-yl)-oxoacetic acid 6-methyl-2-(4-methylphenyl)imidazo[1,2-a]pyridine (45 mmol) and 40 ml ethylene dichloride maintained at a temperature of 20-25° C. was stirred to obtain a solution. To this stirred solution oxalyl chloride (60 mmol) in 10 ml ethylene dichloride was added over a period of 1 hour. To the above reaction mixture triethylamine (59 mmol) was added over 15 minutes. The reaction was further maintained at 30-35° C. by stirring for 3-4 hours. The reaction was monitored by TLC. On completion of the reaction, the reaction mass was cooled and was quenched with 100 ml water. The reaction mass was basified by adding 25 ml of 25% NaOH. The layers were separated. The aqueous layer was extracted with 40 ml ethylene dichloride, cooled and acidified using 20 ml acetic acid (pH 4-5). The solid was filtered, washed with water and dried. Yield: 10.2 gm of the title compound, m.p. 190-195° C. Purity 96% (HPLC).

EXAMPLE 2

(6-Methyl-2-p-tolyl-2,3-dihydro-imidazo[1,2-a]pyridin-3-yl)-oxoacetic acid was prepared according to the method described in Example 1, but by using 130 ml methylene dichloride in place of ethylene dichloride. Yield: 7.9 gm, Purity 97.43% (HPLC).

EXAMPLE 3

(6-Methyl-2-p-tolyl-2,3-dihydro-imidazo[1,2-a]pyridin-3-yl)-oxoacetic acid was prepared according to the method described in Example 1, but by using 130 ml hexane in place of ethylene dichloride. Yield: 5.14 gm, Purity 95.25% (HPLC).

EXAMPLE 4

(6-Methyl-2-p-tolyl-2,3-dihydro-imidazo[1,2-a]pyridin-3-yl)-oxoacetic acid was prepared according to the method described in Example 1, but by using 60 ml toluene in place of ethylene dichloride. Yield: 6.2 gm, Purity 97.27% (HPLC).

EXAMPLE 5

(6-Methyl-2-p-tolyl-2,3-dihydro-imidazo[1,2-a]pyridin-3-yl)-oxoacetic acid was prepared according to the method described in Example 1, but by using 120 ml methyl tert-butyl ether in place of ethylene dichloride. Yield: 10.0 gm, Purity 95.27% (HPLC).

EXAMPLE 6

(6-methyl-2-p-tolyl-imidazo[1,2-a]pyridin-3-yl)acetic acid (Zolpidic acid)

In a clean round bottom flask was charged oxoacetic acid (68 mmol) from example 1, 100 ml of diethylene glycol, hydrazine hydrate (184 mmol) and potassium hydroxide (115 mmol). The reaction mixture was heated to a temperature of 120-180° C. The reaction was monitored by TLC. After completion of the reaction, the reaction mass was cooled to room temperature and 100 ml of water was added. The reaction mass was further cooled to 0-10° C. and the pH was adjusted to 6-6.5 using acetic acid and stirred for 1 hour. The solid obtained was filtered, washed with water and dried in oven at 90-100° C. Yield: 16 gm of the title compound, m.p. 228-230° C. Purity 97% (HPLC).

The invention having been described, it will be readily apparent to those skilled in the art that further changes and modifications in actual implementation of concepts described herein can easily be made or may be learned by practice of the invention, without departing from the scope of the invention as defined by the following claims

The invention claimed is:

1. A process for preparing (6-methyl-2-p-tolyl-imidazo[1,2-a]-pyridin-3-yl)acetic acid (zolpidic acid) of formula (I) which comprises:

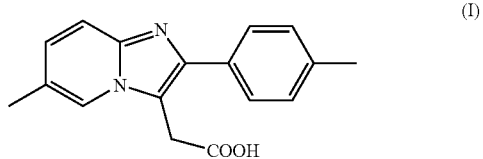

a) reacting 6-methyl-2-(4-methylphenyl)imidazo[1,2-a]pyridine of formula (II) with oxalyl chloride to form (6-methyl-2-p-tolyl-2,3-dihydro-imidazo[1,2-a]pyridin-3-yl)oxoacetyl chloride of formula (III);

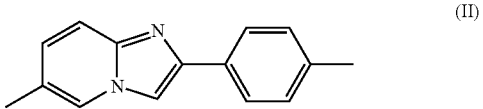

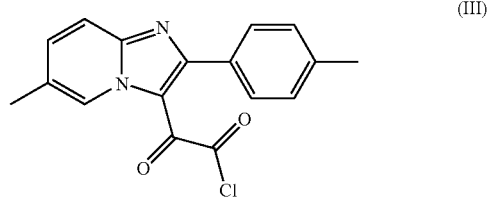

b) converting the compound of formula (III) to (6-methyl-2-p-tolyl-2,3-dihydro-imidazo[1,2-a]pyridin-3-yl)-oxoacetic acid of formula (IV) or its salt; and

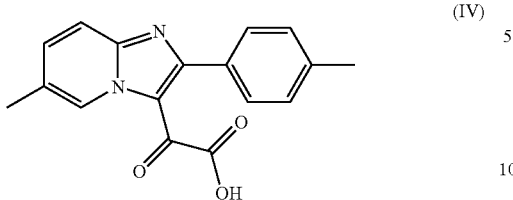

(IV)

c) reacting the acid of formula (IV) or its salt with hydrazine in presence of a glycol and base to form 6-methyl-2-p-tolyl-imidazo[1,2-a]pyridin-3-yl)acetic acid (zolpidic acid).

2. The process according to claim 1 wherein step b) is carried out either by reacting the compound of formula (III) with water or by reacting the compound of formula (III) with water and a base.

3. The process according to claim 2 wherein the base is selected from sodium hydroxide, potassium hydroxide, sodium carbonate or potassium carbonate.

4. The process according to claim 3 wherein the base is sodium hydroxide or potassium hydroxide.

5. The process according to claim 1 wherein the glycol in step c) is selected from ethylene glycol or diethylene glycol.

6. The process according to claim 1 wherein the step c) is carried out at a temperature of 120- 200 ° C.

7. The process according to claim 6 wherein the temperature in step c) is from 130- 160 ° C.

8. The process according to claim 7 wherein the temperature in step c) is about 150 ° C.

9. The process according to claim 1 wherein step a) is carried out by reacting the compound of formula (II) with oxalyl chloride in the presence of a solvent and a base at a temperature of about 15-30 ° C.

10. The process according to claim 9 wherein the solvent is ethylene dichloride, methyl tert-butyl ether, methylene dichloride, hexane, or toluene, and the base is triethylamine, potassium bicarbonate, sodium bicarbonate, potassium carbonate, or sodium carbonate.

11. The process according to claim 10 wherein the solvent is ethylene dichloride or methylene dichloride and the base is triethylamine.

12. The process according to claim 1 wherein the glycol in step c) is diethylene glycol and the base in step c) is potassium hydroxide.

13. The process according to claim 2 wherein the base is a hydroxide or carbonate of an alkali or an alkaline metal.

14. A process for preparing (6-methyl2-p-tolyl-2,3-dihydro-imidazo[1,2-a]-pyridin-3-yl)-oxoacetic acid of formula (IV) or its salt, which comprises:

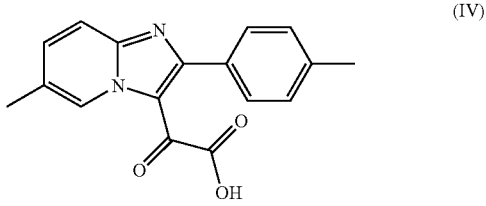

(IV)

a) reacting 6-methyl-2-(4-methylphenyl)imidazo[1,2-a]pyridine of formula (II) with oxalyl chloride to form (6-methyl-2-p-tolyl-2,3-dihydro-imidazo[1,2-a]pyridin-3-yl)-oxoacetyl chloride of formula (III); and

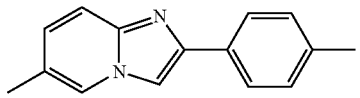

(II)

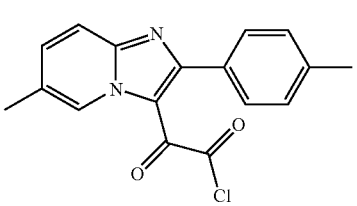

(III)

b) converting the compound of formula (III) to (6-methyl-2-p-tolyl-2,3-dihydro-imidazo[1,2-a]pyridin-3-yl)-oxoacetic acid of formula (IV) or its salt.

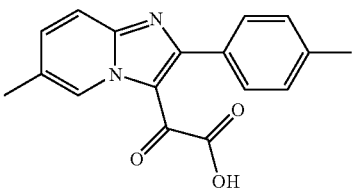

(IV)

15. The process according to claim 14 wherein step a) is carried out by reacting the compound of formula (II) with oxalyl chloride in the presence of a solvent and a base at a temperature of about 15-30 ° C.

16. The process according to claim 15 wherein the solvent is ethylene dichloride, methyl tert-butyl ether, methylene dichloride, hexane, or toluene, and the base is triethylamine, potassium bicarbonate, sodium bicarbonate, potassium carbonate, or sodium carbonate.

17. The process according to claim 16 wherein the solvent is ethylene dichloride or methylene dichloride and the base is triethylamine.

18. The process according to claim 14 wherein step b) is carried out either by reacting the compound of formula (III) with water or by reacting the compound of formula (III) with water and a base.

19. The process according to claim 18 wherein the base is a hydroxide or carbonate of an alkali or an alkaline metal.

20. The process according to claim 19 wherein the base is sodium hydroxide, potassium hydroxide, sodium carbonate or potassium carbonate.

21. The process according to claim 20 wherein the base is sodium hydroxide or potassium hydroxide.

22. A compound [6-methyl-2-p-tolyl-2,3-dihydro-imidazo[1,2-a]-pyridin-3-yl)-oxoacetic acid] having formula (IV) or its salt.

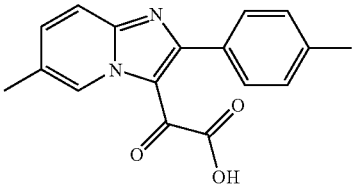

(IV)

23. The compound of claim 22 wherein the salt of compound (IV) is the sodium or potassium salt.

\* \* \* \* \*

UNITED STATES PATENT AND TRADEMARK OFFICE
CERTIFICATE OF CORRECTION

PATENT NO.      : 8,183,377 B2                                          Page 1 of 1
APPLICATION NO. : 11/990880
DATED           : May 22, 2012
INVENTOR(S)     : Alok et al.

It is certified that error appears in the above-identified patent and that said Letters Patent is hereby corrected as shown below:

On title page 1, in column 1, under "Inventors", line 5, delete "Jadhay" and insert --Jadhav--, therefor On title page 1, in column 1, under "Assignee", line 2, delete "Mumbaie" and insert --Mumbai--, therefor In the Specification In column 1, line 35, delete "al," and insert --al.,--, therefor In column l, line 45, delete "phosphorus-containing" and insert --phosphorus- containing--, therefor In column 1, line 45, delete "'875" and insert --'875--

In column 2, line 34, delete "(VI)" and insert --(VII)--, therefor

In column 3, line 23, delete "(VI)" and insert --(VII)--, therefor

In column 3, line 3-14, delete " 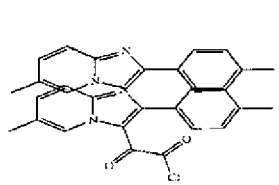 " and insert -- 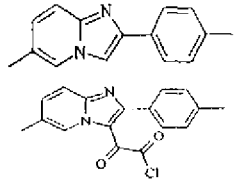 --, therefor In column 4, line 56, after "and", insert --¶--, therefor In column 5, line 2, delete "(II)" and insert --(III)--, therefor Signed and Sealed this
Ninth Day of December, 2014

Michelle K. Lee
*Deputy Director of the United States Patent and Trademark Office*